(12) United States Patent
Grambergs

(10) Patent No.: US 10,639,388 B1
(45) Date of Patent: May 5, 2020

(54) INTERNAL LUMEN DISINFECTION DEVICE

(71) Applicant: Richard Grambergs, Suwanee, GA (US)

(72) Inventor: Richard Grambergs, Suwanee, GA (US)

(*) Notice: Subject to any disclaimer, the term of this patent is extended or adjusted under 35 U.S.C. 154(b) by 0 days.

(21) Appl. No.: 16/395,871

(22) Filed: Apr. 26, 2019

(51) Int. Cl.
*A61L 2/10* (2006.01)
*A61L 2/24* (2006.01)
*A61L 2/00* (2006.01)

(52) U.S. Cl.
CPC ............. *A61L 2/10* (2013.01); *A61L 2/0047* (2013.01); *A61L 2/24* (2013.01); *A61L 2202/11* (2013.01); *A61L 2202/14* (2013.01); *A61L 2202/24* (2013.01)

(58) Field of Classification Search
CPC . A61L 2/10; A61L 2/0047; A61L 2/24; A61L 2202/11; A61L 2202/14; A61L 2202/24
USPC .............. 250/453.11, 454.11, 455.11, 504 R, 250/504 H
See application file for complete search history.

(56) References Cited

U.S. PATENT DOCUMENTS

| | | |
|---|---|---|
| 4,755,292 A | 7/1988 | Merriam |
| 5,637,877 A | 6/1997 | Sinofsky |
| 6,461,569 B1 | 10/2002 | Boudreaux |
| 6,730,265 B2 | 5/2004 | Horton |
| 6,766,097 B2 | 7/2004 | Horton |
| 7,175,806 B2 | 2/2007 | Deal et al. |
| 7,829,016 B2 | 11/2010 | Deal et al. |
| 8,203,124 B2 | 6/2012 | Havens et al. |
| 8,951,468 B1 | 2/2015 | Perry |
| 9,925,287 B1 | 3/2018 | Zaborsky et al. |
| 2005/0220665 A1* | 10/2005 | Ding ............... A61B 1/123 422/20 |
| 2014/0271348 A1* | 9/2014 | Deal ............... A61L 2/00 422/3 |
| 2017/0182194 A1* | 6/2017 | Shin ............... A61L 2/10 |
| 2019/0008607 A1* | 1/2019 | Bauco ............. A61L 2/10 |
| 2019/0038789 A1* | 2/2019 | Kang .............. A61B 1/122 |

* cited by examiner

*Primary Examiner* — Nicole M Ippolito
(74) *Attorney, Agent, or Firm* — David L. King

(57) ABSTRACT

An internal lumen disinfection device has a case, a power source, a UV lamp, a plurality of light transmitting connectors and at least one light transmitting tube. The case has a lid or cover and an elongated base configured to hold one or more surgical endoscopes in a disinfecting portion and a power and UV lamp housing portion adjacent the disinfecting portion. A battery or electrical power source is in the housing portion. The UV lamp is in the housing portion connected to and powered by the power source. The case has a divider wall with openings for passing UV light. The plurality of light transmitting connectors are each affixed to the divider wall at an opening. At least one light transmitting tube, preferably a plurality of light transmitting tubes are used to disinfect lumens of endoscopes.

19 Claims, 6 Drawing Sheets

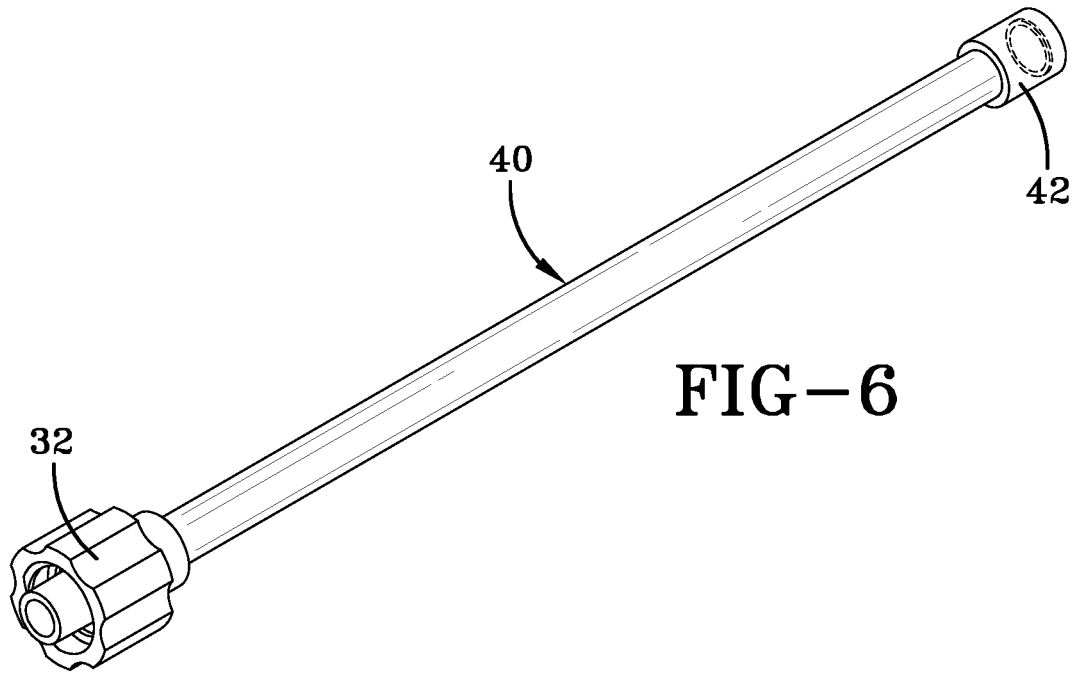
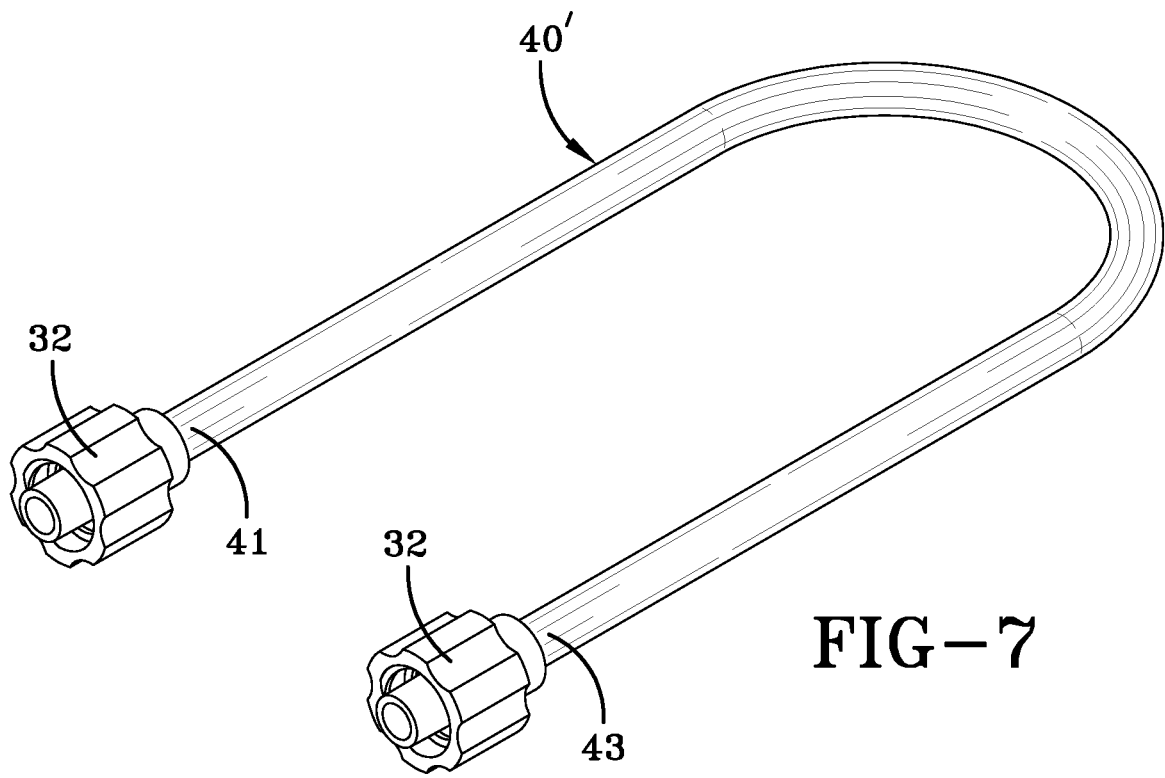

INTERNAL LUMEN DISINFECTION DEVICE

TECHNICAL FIELD

The present invention relates to an improved Ultra Violet light sterilization/disinfection device and method to disinfect elongated tubes such as endoscopes.

BACKGROUND OF THE INVENTION

Ultra-violet lights also known as UV lamps are known to provide a highly efficient way to germicidally remove pathogens like viruses and bacteria. UV sterilization has been used in treating air in duct systems, in treating water or other fluids, and in a number of uses in disinfecting surfaces.

The use of UV lights has to be achieved in such a way to avoid damage to the operator of the device. Eye damage and skin cancers could result from prolonged exposure, in the case of vision, even short exposures can be harmful.

In U.S. Pat. No. 5,637,877 issued Jun. 10, 1997, inventor Edward L. Sinofsky disclosed in "Ultraviolet sterilization of instrument lumens" a way to use diffuse UV radiation via optical fibers to deliver cytotoxic radiation to the inner lumen surface to sterilize any biological agents which may be present within the instrument lumen. Sinofsky discloses a number of ways the optical fibers can be used in combination with a diffuser tip assembly coupled to it, and the combination fits inside the lumen. A goal of the inventor was to provide a safe and reusable device.

The present invention is an improvement over this prior art device that allows the device to be made cheaply and efficiently so the sterilizing or disinfection apparatus is reusable while flexible light tubes are made disposable to be discarded after use.

Another objective is to make a tube device that allows for quick attachment to a UV source and a quick detachment wherein only the tube assembly is discarded.

Another objective is to provide the apparatus with a protective feature wherein the emitted UV radiation is contained inside the apparatus and cannot be used unless the UV radiation is sealed inside the container. These and other benefits are discussed in the details of the invention as disclosed herein.

SUMMARY OF THE INVENTION

An internal lumen disinfection device has a case, a power source, a UV lamp, a plurality of light transmitting connectors and at least one light transmitting tube. The case has a lid or cover and an elongated base configured to hold one or more surgical endoscopes in a disinfecting portion and a power and UV lamp housing portion adjacent the disinfecting portion. A battery or electrical power source is in the housing portion. The UV lamp is in the housing portion connected to and powered by the power source. The case has a divider wall with openings for passing UV light into the storage portion. The plurality of light transmitting connectors are each affixed to the divider wall at an opening. At least one light transmitting tube, preferably a plurality of light transmitting tubes are used. Each of the light transmitting tubes have a light transmitting connector end for attaching the connector end of the at least one light transmitting tube to a connector on the divider wall. The light transmitting tube has a length sufficient for internally disinfecting a lumen of an endoscope. The connector is a threaded fitting and the connector end of the tube is a complementary fitting configured for attachment and detachment. The at least one light transmitting tube is flexible along its length. Along the length of the tube is translucent or transparent for passing disinfecting UV light, the length being a flexible polymer or glass, preferably a fiber optic tube. The at least one light transmitting tube has a second end. The second end can be a plug with a light reflecting mirror like surface.

Alternatively, the at least one light transmitting tube has a length sufficient to pass through two endoscopes by bending the tube between the first endoscope and the second endoscope allowing disinfecting both lumens by extending back through the second endoscope and wherein the second end has a connector end for connecting to a connector on the divider wall.

In one embodiment, the case is AC powered and has a plug-in cord.

The case has a switch to turn on or off the UV lamp. The switch has a timer. The the lid or cover can be hinged to the elongated base. The case can have a printer device to record and print disinfection times. The lid or cover also can have a UV filter in the shape of a lit logo to visually alert users when the UV lamp is lit. The case or the lid or cover has a button which disables the UV lamp until the lid or cover is closed onto the case. The second end of the at least one light transmitting tube further includes a cleaning brush or cleaning cloth. The case further can have a kit of one or more light transmitting tubes in a package. Each light transmitting tube can be disposable configured for one-time use.

Definitions

As used herein and in the claims:

UV Sterilization/disinfection: Ultraviolet light exists within the spectrum of light between 10 and 400 nm. The germicidal range of UV is within the 100-280 nm wavelengths, known as UV-C, with the peak wavelength for germicidal activity being 265 nm. This range of UV light is absorbed by the DNA and RNA of microorganisms, which causes changes in the DNA and RNA structure. Ultraviolet germicidal irradiation (UVGI) is a disinfection method that uses short-wavelength ultraviolet (UV-C) light to kill or inactivate microorganisms by destroying nucleic acids and disrupting their DNA, leaving them unable to perform vital cellular functions. Disinfection times are fast, with a typical disinfection cycle lasting about 15 minutes. This allows for extremely fast turnover times for items being disinfected. Ultraviolet technology is a non-chemical approach to disinfection. In this method of disinfection, nothing is added which makes this process simple, inexpensive and requires very low maintenance. Ultraviolet purifiers utilize germicidal lamps that are designed and calculated to produce a certain dosage of ultraviolet, usually at least 16,000 microwatt seconds per square centimeter but many units actually have a much higher dosage.

BRIEF DESCRIPTION OF THE DRAWINGS

The invention will be described by way of example and with reference to the accompanying drawings in which:

FIG. 6 is a plan view of a first embodiment light transmitting tube with a reflective or mirrored plug at a second end.

FIG. 7 is an alternative embodiment light transmitting tube having a length sufficient to disinfect two endoscope lumens, as shown the tube has a connector at each end and can be bent to allow attachment to the divider wall connectors.

DETAILED DESCRIPTION OF THE INVENTION

Figure 1:
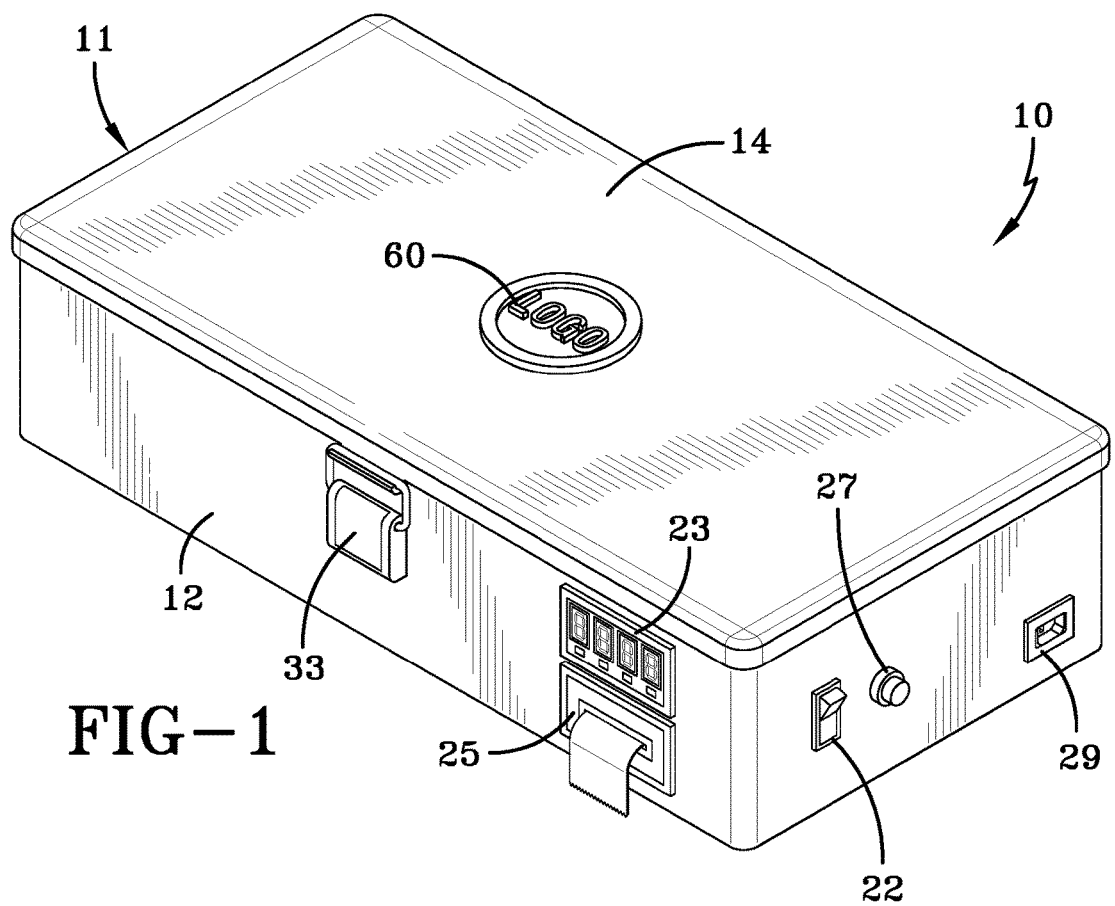
FIG. 1 is a perspective view of the internal lumen disinfection device of the present invention.
Figure 2:
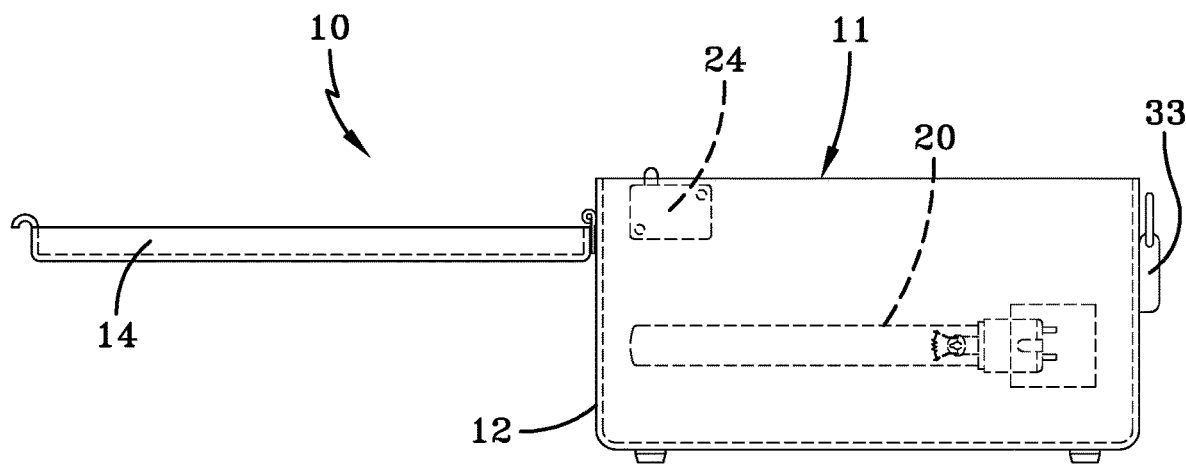
FIG. 2 is an end view of the device of FIG. 1 showing the case with the lid or cover open hinged to the elongated base.

The present invention is an internal lumen disinfection device 10. As shown in FIGS. 1-4, the device 10 includes a case 11 with a lid or cover 14 and an elongated base 12. The lid or cover 14 can be provided with a logo 60 that allows visually detecting light when the UV lamp 20 is on. This logo 60 is configured to be visibly lit, but with sufficient shielding to prevent eye damage. Optionally, the device 10 could have a power on indicator light 27 as shown in FIG. 1.

Figure 3:
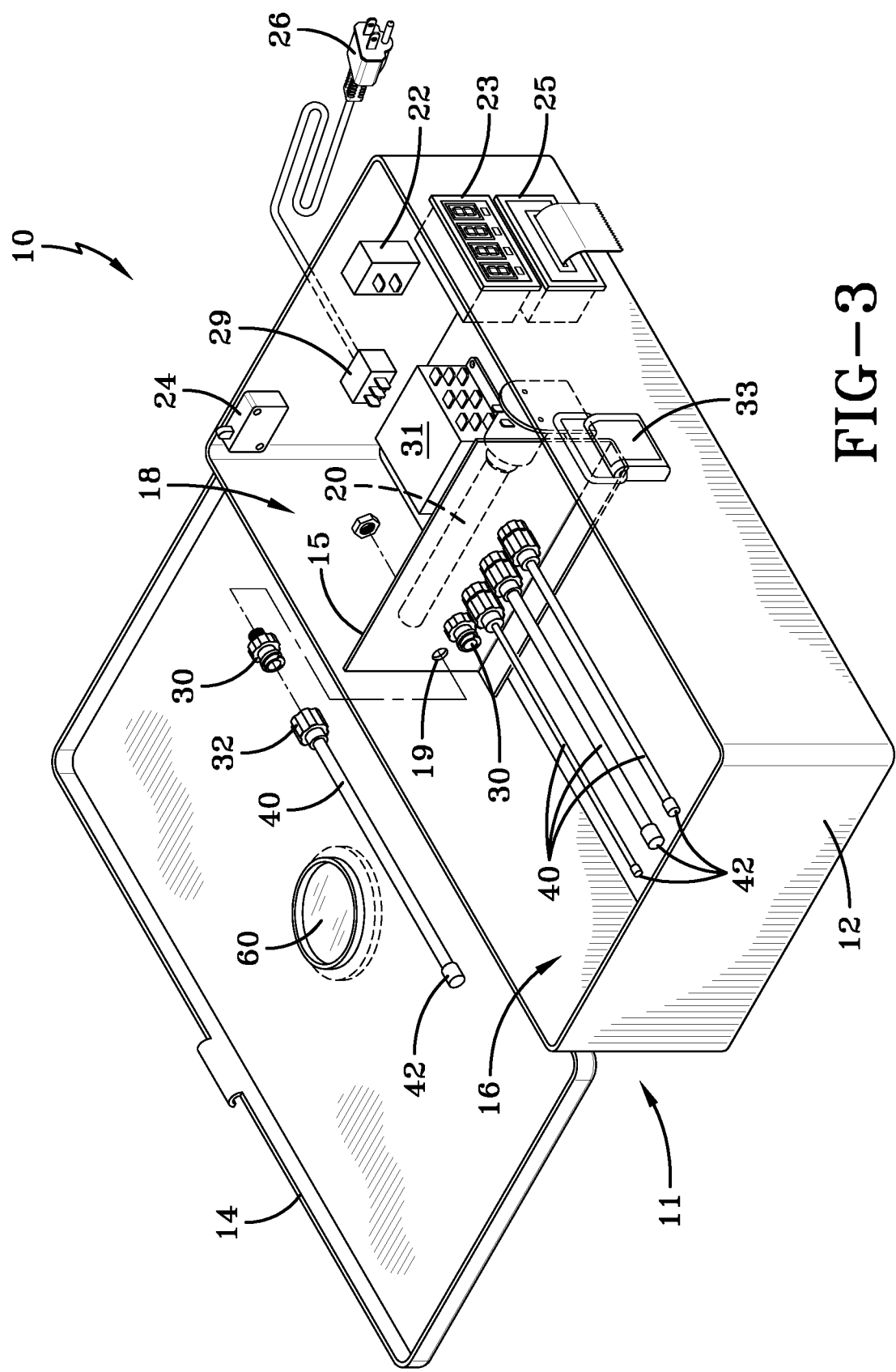
FIG. 3 is a perspective view of the device showing the case open showing the disinfecting portion holding endoscopes and a UV lamp separated b y a divider wall.

As shown in FIGS. 1 and 3, the case 11 can have a port 29 for attaching a length of electrical cord and plug 26 to connect to an electrical outlet to provide power. Alternatively, the device 10 can be powered by a rechargeable battery if so desired.

After an exposure to the UV light, the inside surfaces of the lumen will be disinfected by the UV radiation exposure over a selected time. The operator can select the time by setting a timer 23, once finished, the UV lamp 20 will shut off automatically. A printer 25 inside the case 11 can be used to print a receipt showing the date and time of threating the endoscope with UV radiation.

Preferably, as shown in FIG. 3, the case 11 has a safety switch 24 on the body 12 that must be depressed by the lid or cover 14 when closed before allowing the UV lamp switch 22 to turn on the UV lamp 20. The device 10 can optionally include a controller housing 31 where a PC board and voltage regulator could be stored.

As shown in FIG. 3, the elongated base 12 is configured to hold one or more surgical endoscopes in a disinfecting portion 16. Adjacent the portion 16 is a power and UV lamp housing portion 18. The two portions 16 and 18 are separated by a divider wall 15 with openings 19 for passing UV light into the disinfecting portion 16. The lid or cover 14 can be hinged to the base 12. Alternatively, the lid or cover 14 can be affixed to the base 12 with another suitable method such as a latch type closure 33.

Figure 4:
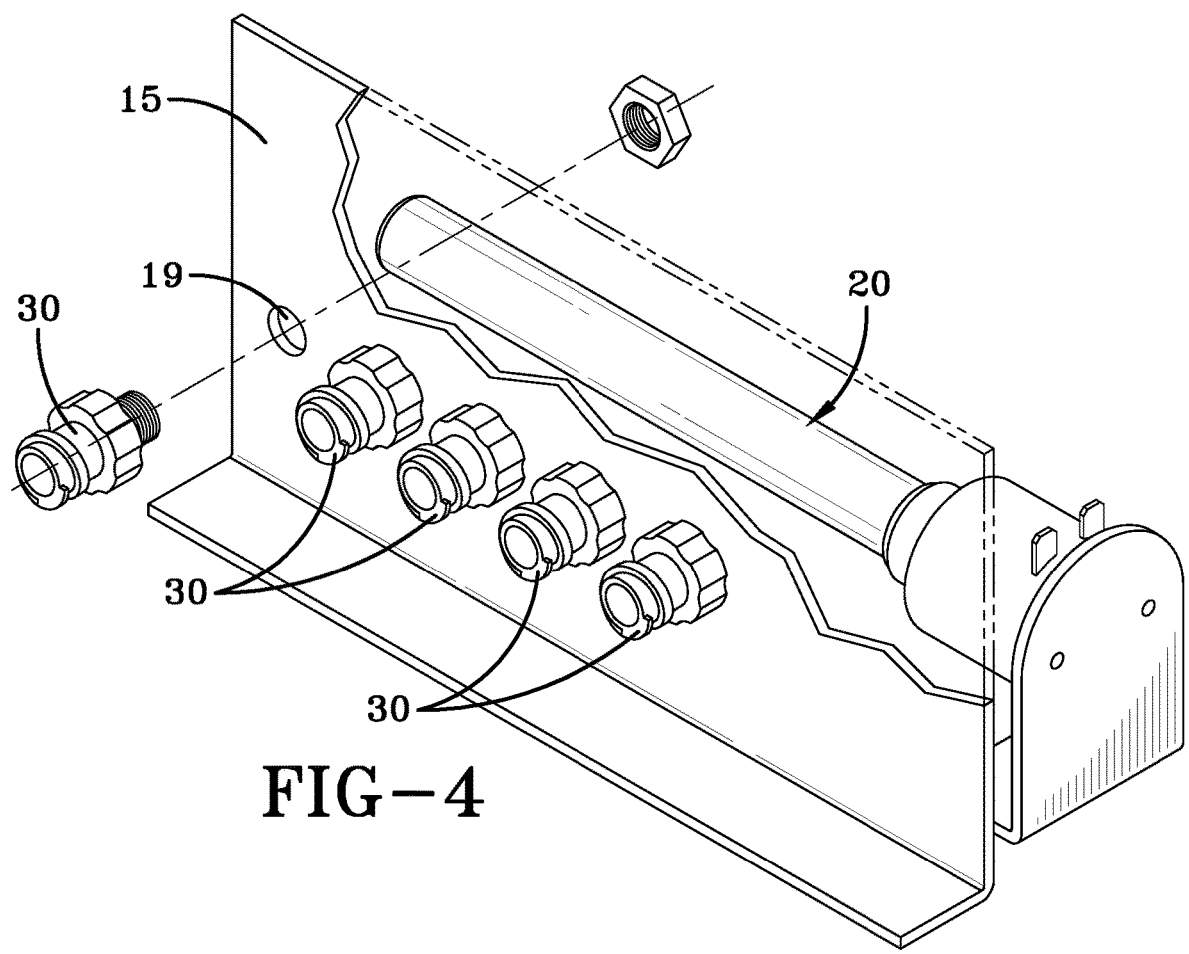
FIG. 4 is a perspective view of the divider wall with a plurality of light transmitting connectors and the UV lamp positioned behind the divider wall.

As shown in FIG. 4, the divider wall 15 has a plurality of openings 19. Each opening 19 has a light transmitting connector 30 affixed thereto for transmitting light from the UV lamp 20.

Figure 5:
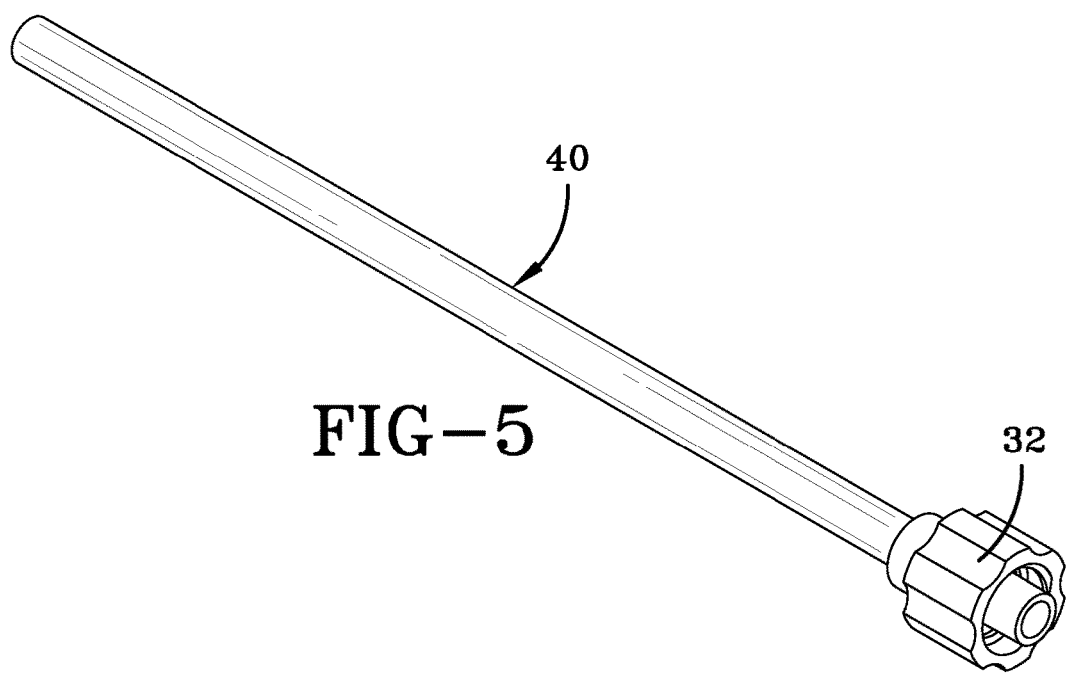
FIG. 5 is a plan view of a light transmitting tube with a connector end at a first attachment end.

As shown in FIG. 5, one of the at least one light transmitting tubes 40 is shown. Each of the light transmitting tubes 40 has a light transmitting connector end 32. The connector end 32 can be attached to the light transmitting tube 40 after inserting the light transmitting tube 40 into the endoscope 2. The connector end 32 attaches to a complementary connector 30 on the divider wall 15. Each light transmitting tube 40 has a length sufficient for internally disinfecting a lumen of an endoscope 2. The endoscopes 2 are shown schematically as straight tubes for simplicity. It is understood these devices can be curved, flexible or rigid.

As shown, the connector 30 can be a threaded fitting and the connector end 32 is a complementary fitting configured to be attached and detached to the connectors 30 at the divider wall 15. One type of fitting useful for this application is commonly referred to as Luer Lock fittings. The light transmitting tube 40 can be a flexible polymer or glass material, including quartz glass or its equivalent, capable of allowing UV light to pass along the entire length radially outwardly. The light transmitting tube 40 can be a fiber optic type material that is clear or translucent capable of passing the UV radiation all the way along the interior lumen surface of the endoscope being disinfected.

Figure 8:
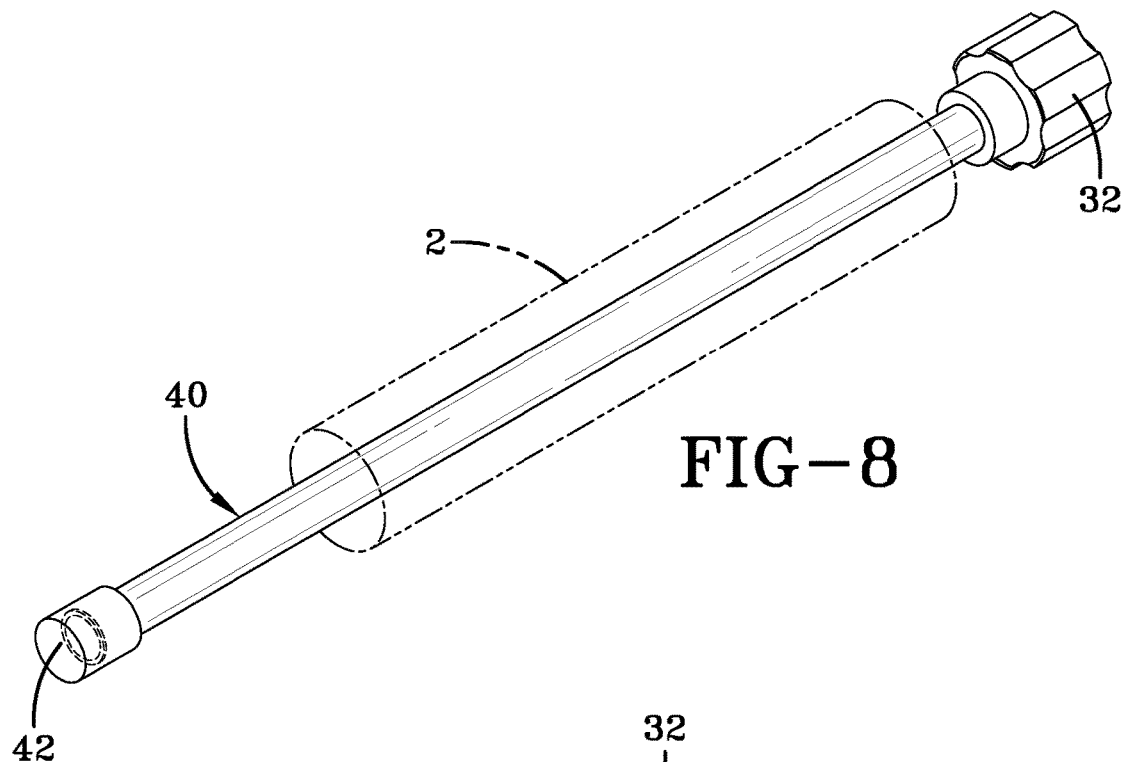
FIG. 8 shows the first embodiment light transmitting tube inside a lumen of an endoscope.

In FIG. 6, the light transmitting tube 40 has a plug end 42. The plug end 42 is preferably a mirrored or shiny surface to reflect the UV light back when inside the lumen inside of the endoscopes 2 as shown in FIG. 8.

Figure 9:
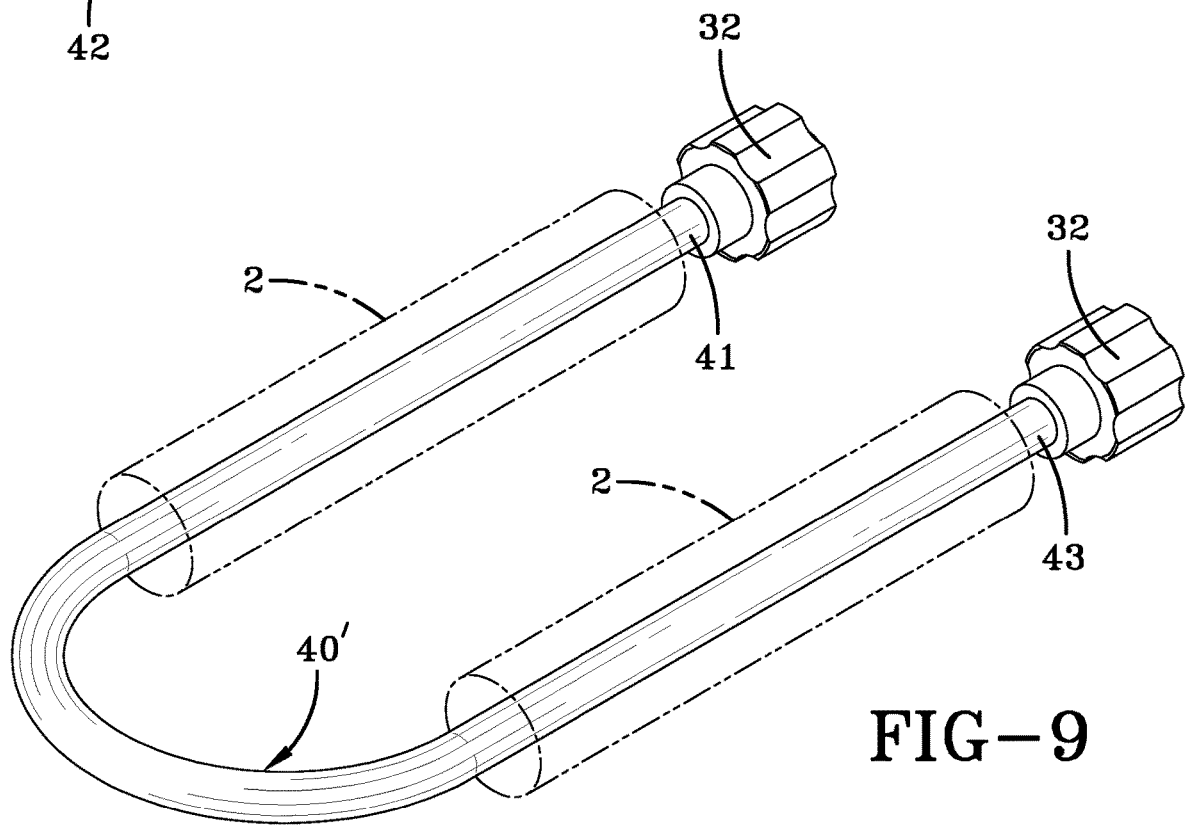
FIG. 9 is a view of the second or alternative tube showing inside the lumens of two endoscopes.

In FIG. 7, the light transmitting tube 40' is doubled in length. This extra length allows the tube to disinfect two endoscopes simultaneously, see FIG. 9. In this embodiment, both ends 41, 43 of the tube 40' have the connector ends 32 to be attached to connectors 30 of the divider wall 15. One or both of the connector ends 32 is detachable to insert tube 40' into an endoscope 2, then reattached after insertion.

Figure 10:
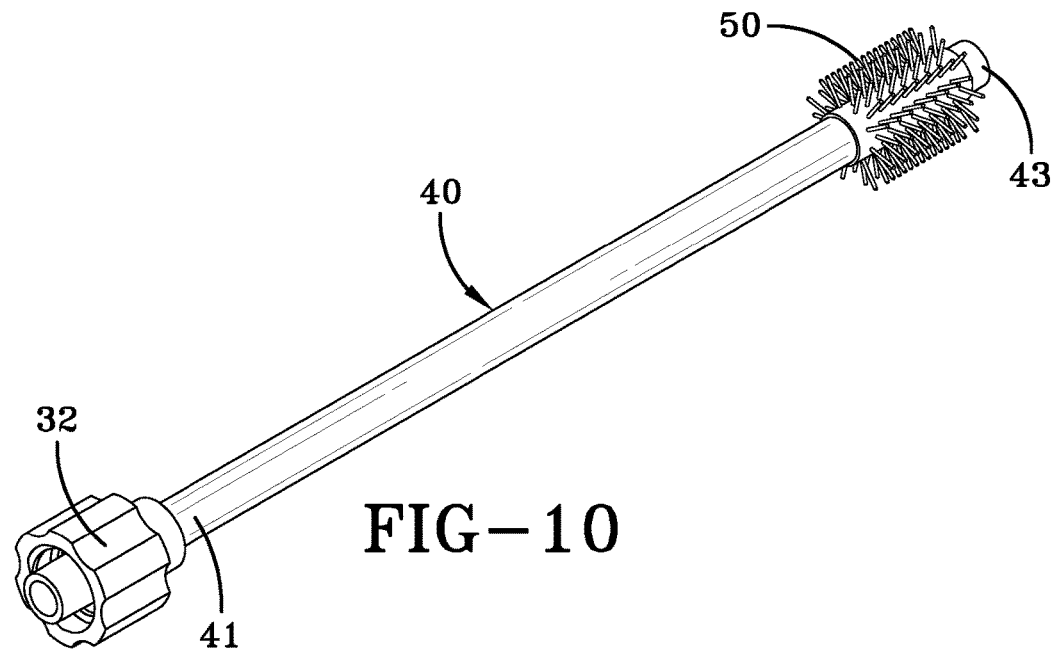
FIG. 10 is a third embodiment tube having a lumen cleaning brush at the second end.

In still a further embodiment shown in FIG. 10, the second end 43 of a tube 40 can have an annular or ring type brush 50 attached to clean the lumen of the endoscope 2 on insertion.

The size of the device 10 is roughly 6 inches in height, 12 inches in width and 30 inches in length. These sizes can be varied. The case 11 with all its features is reusable, however, the tubes 40 can be provided as disposable one-time use components due to the low cost of manufacture.

Figure 11:
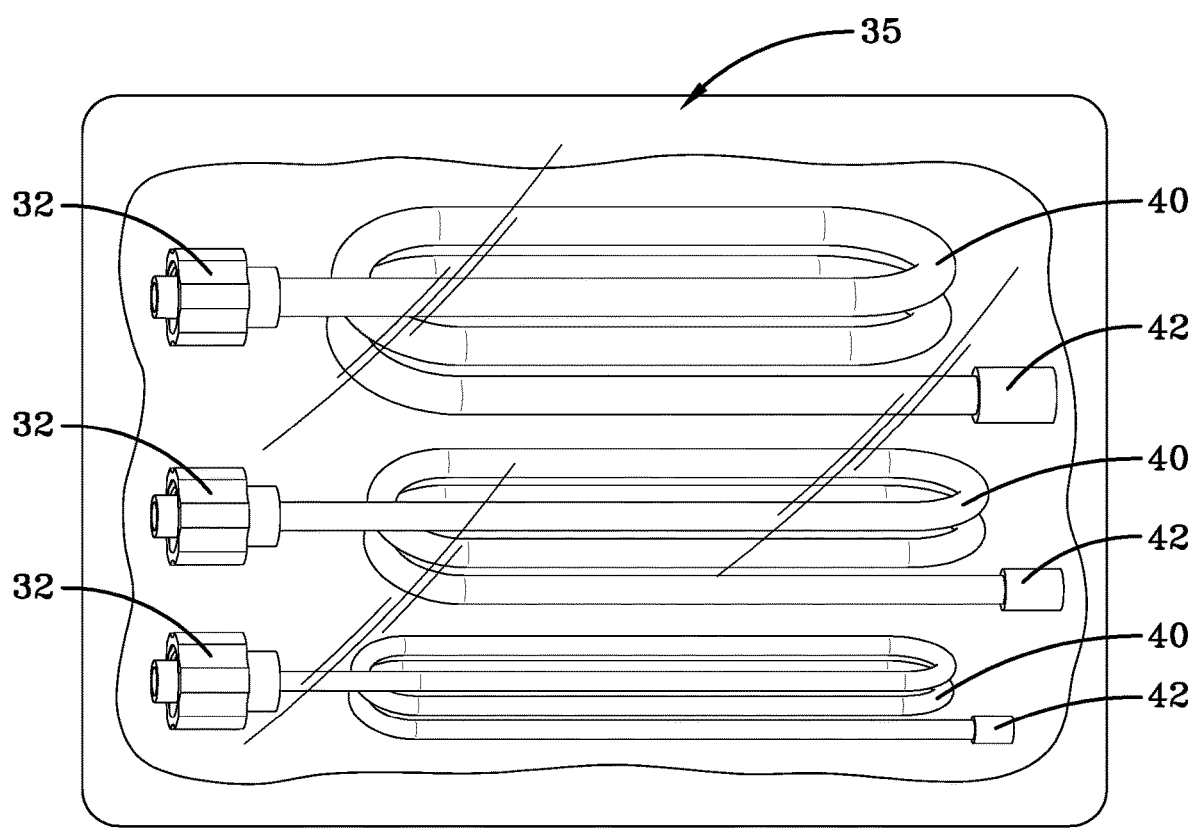
FIG. 11 is a perspective view of an exemplary pouch or package containing disposable light transmitting tubes.

FIG. 11 shows an exemplary view of disposable tubes 40 of varying sizes for use with the present invention packaged in a pouch or package 35.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. An internal lumen disinfection device comprises:
   a case having a lid or cover and an elongated base configured to hold one or more surgical endoscopes in a disinfecting portion, a power and UV lamp housing portion adjacent the disinfecting portion;
   a battery or electrical power source in the housing portion;

a UV lamp in the housing portion connected to the power source; the case having a divider wall with openings for passing UV light into the disinfecting portion;

a plurality of light transmitting connectors each affixed to the divider wall at an opening;

at least one light transmitting tube; and wherein each of the light transmitting tubes have a light transmitting connector end for attaching the connector end of the at least one light transmitting tube to a connector on the divider wall, the light transmitting tube having a length sufficient for internally disinfecting a lumen of an endoscope.

2. The internal lumen disinfection device of claim 1 wherein the connector is a threaded fitting and the connector end of the tube is a complementary fitting configured for attachment and detachment.

3. The internal lumen disinfection device of claim 1 wherein the at least one light transmitting tube is flexible along the length.

4. The internal lumen disinfection device of claim 3 wherein the length is translucent or transparent for passing disinfecting UV light.

5. The internal lumen disinfection device of claim 4 wherein the length is a flexible polymer or glass.

6. The internal lumen disinfection device of claim 5 wherein the length is a fiber optic tube.

7. The internal lumen disinfection device of claim 1 wherein the at least one light transmitting tube has a second end.

8. The internal lumen disinfection device of claim 7 wherein the second end is a plug with a light reflecting mirror like surface.

9. The internal lumen disinfection device of claim 7 wherein the at least one light transmitting tube has a length sufficient to pass through two endoscopes by bending the tube between the first endoscope and the second endoscope allowing disinfecting both lumens by extending back through the second endoscope and wherein the second end has a connector end for connecting to a connector on the divider wall.

10. The internal lumen disinfection device of claim 1 wherein the case is AC powered and has a plug-in cord.

11. The internal lumen disinfection device of claim 1 wherein the case has a switch to turn on or off the UV lamp.

12. The internal lumen disinfection device of claim 11 wherein the switch has a timer.

13. The internal lumen disinfection device of claim 1 wherein the lid or cover is hinged to the elongated base.

14. The internal lumen disinfection device of claim 1 wherein the case has a printer device to record and print disinfection times.

15. The internal lumen disinfection device of claim 1 wherein the lid or cover has a UV filter in the shape of a lit logo to visually alert users when the UV lamp is lit.

16. The internal lumen disinfection device of claim 1 wherein the case or the lid or cover has a button which disables the UV lamp until the lid or cover is closed onto the case.

17. The internal lumen disinfection device of claim 1 wherein the second end of the at least one light transmitting tube further includes a cleaning brush or cleaning cloth.

18. The internal lumen disinfection device of claim 1 wherein the case further comprises a kit of one or more light transmitting tubes in a package.

19. The internal lumen disinfection device of claim 1 wherein each light transmitting tube is disposable configured for one-time use.

* * * * *